US012308876B2

(12) United States Patent
Murata

(10) Patent No.: US 12,308,876 B2
(45) Date of Patent: May 20, 2025

(54) WIRELESS TERMINAL AND WIRELESS SYSTEM

(71) Applicant: KELK Ltd., Kanagawa (JP)

(72) Inventor: Tomonori Murata, Kanagawa (JP)

(73) Assignee: KELK Ltd., Kanagawa (JP)

( * ) Notice: Subject to any disclaimer, the term of this patent is extended or adjusted under 35 U.S.C. 154(b) by 264 days.

(21) Appl. No.: 17/879,081

(22) Filed: Aug. 2, 2022

(65) Prior Publication Data

US 2023/0055689 A1 Feb. 23, 2023

(30) Foreign Application Priority Data

Aug. 17, 2021 (JP) .................................. 2021-132925

(51) Int. Cl.
*H04B 1/38* (2015.01)
*H02J 50/00* (2016.01)

(52) U.S. Cl.
CPC .............. *H04B 1/38* (2013.01); *H02J 50/001* (2020.01)

(58) Field of Classification Search
CPC .... G06F 1/263; G01N 33/2888; G08C 17/02; H02J 50/001; H04B 1/38; H04Q 2209/40; H04Q 2209/886; H04Q 9/00; H10N 10/17
See application file for complete search history.

(56) References Cited

U.S. PATENT DOCUMENTS

| 11,274,956 | B2 * | 3/2022 | Du | G01F 23/266 |
| 2014/0176041 | A1 * | 6/2014 | Sun | G06F 1/32 |
| | | | | 320/101 |
| 2020/0325657 | A1 * | 10/2020 | Takami | E02F 9/267 |
| 2021/0176318 | A1 * | 6/2021 | Darrah | G01D 21/02 |
| 2023/0027588 | A1 * | 1/2023 | Hua | G06F 3/0679 |

FOREIGN PATENT DOCUMENTS

| JP | 6616251 B2 | 12/2019 |
| JP | 2020137403 A | 8/2020 |

* cited by examiner

*Primary Examiner* — Nguyen T Vo
(74) *Attorney, Agent, or Firm* — Fish & Richardson P.C.

(57) ABSTRACT

A wireless terminal includes a memory that stores a parameter, a microcomputer that operates in an operation mode, which is predetermined, on the basis of the parameter, and a wireless communication device that wirelessly receives a change command of the parameter. When the change command is wirelessly received, the microcomputer suspends the operation and changes the parameter on the basis of the change command.

9 Claims, 5 Drawing Sheets

WIRELESS TERMINAL AND WIRELESS SYSTEM

CROSS-REFERENCE TO RELATED APPLICATION(S)

The present application claims priority to and incorporates by reference the entire contents of Japanese Patent Application No. 2021-132925 filed in Japan on Aug. 17, 2021.

BACKGROUND OF THE INVENTION

1. Field of the Invention

The present disclosure relates to a wireless terminal and a wireless system.

2. Description of the Related Art

In a technical field related to a wireless terminal, a wireless sensor terminal as disclosed in Japanese Patent No. 6616251 is known.

The wireless terminal includes a microcomputer. In a case where parameters of the microcomputer are wirelessly changed, there is a need for a technique to reduce power consumption.

An object of the present disclosure is to reduce power consumption.

SUMMARY OF THE INVENTION

It is an object of the present invention to at least partially solve the problems in the conventional technology.

According to an aspect of the present invention, a wireless terminal comprises: a memory that stores a parameter; a microcomputer that operates in an operation mode, which is predetermined, on a basis of the parameter; and a wireless communication device that wirelessly receives a change command of the parameter, wherein the microcomputer suspends the operation when the change command is wirelessly received, and changes the parameter on a basis of the change command.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, embodiments according to the present disclosure will be described with reference to the drawings, but the present disclosure is not limited to the embodiments. The components of the embodiments to be described below can be appropriately combined. Alternatively, some components may not be used.

Wireless System

Figure 1:
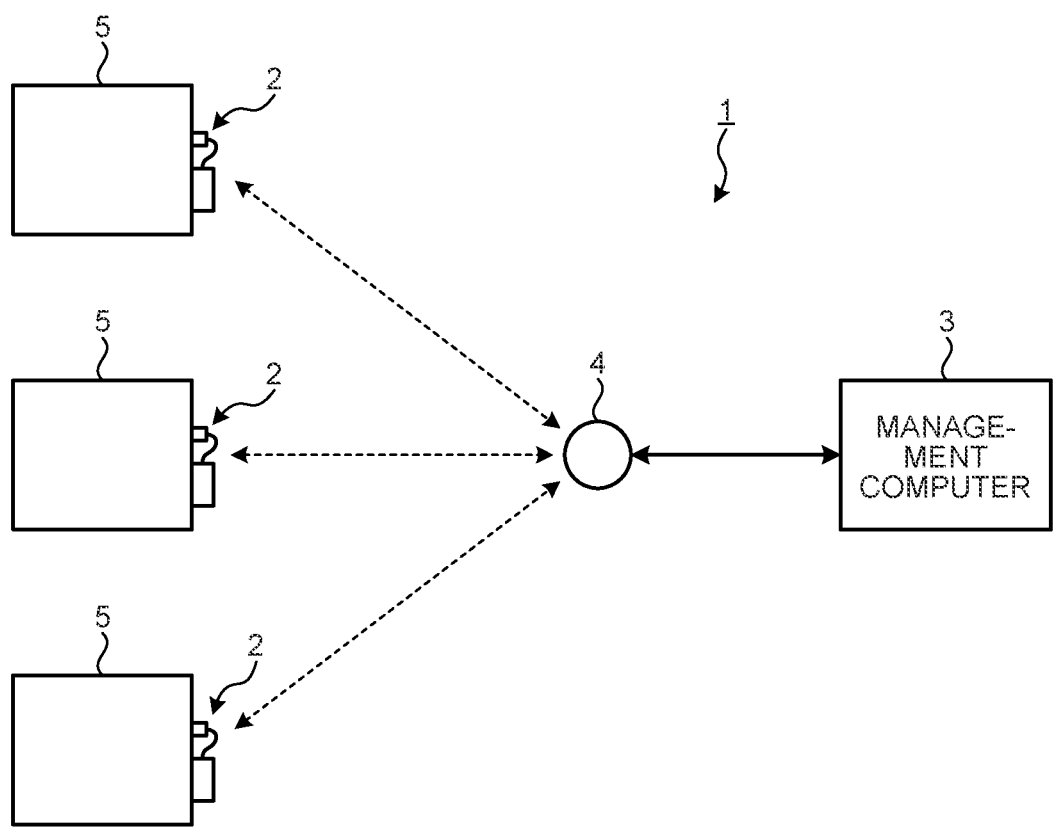
FIG. 1 is a diagram schematically illustrating a wireless system according to an embodiment.

FIG. 1 is a diagram schematically illustrating a wireless system 1 according to an embodiment. The wireless system 1 includes a wireless terminal 2 and a management computer 3. The wireless terminal 2 is provided in plural. The management computer 3 wirelessly communicates with each of the wireless terminals 2 via a communication system 4.

In the embodiment, the wireless terminal 2 is installed in a hydraulic device 5. The wireless terminal 2 detects hydraulic oil in the hydraulic device 5. In the example illustrated in FIG. 1, one wireless terminal 2 is provided for each of the hydraulic devices 5. A plurality of wireless terminals 2 may be provided in one hydraulic device 5.

Wireless Terminal

Figure 2:
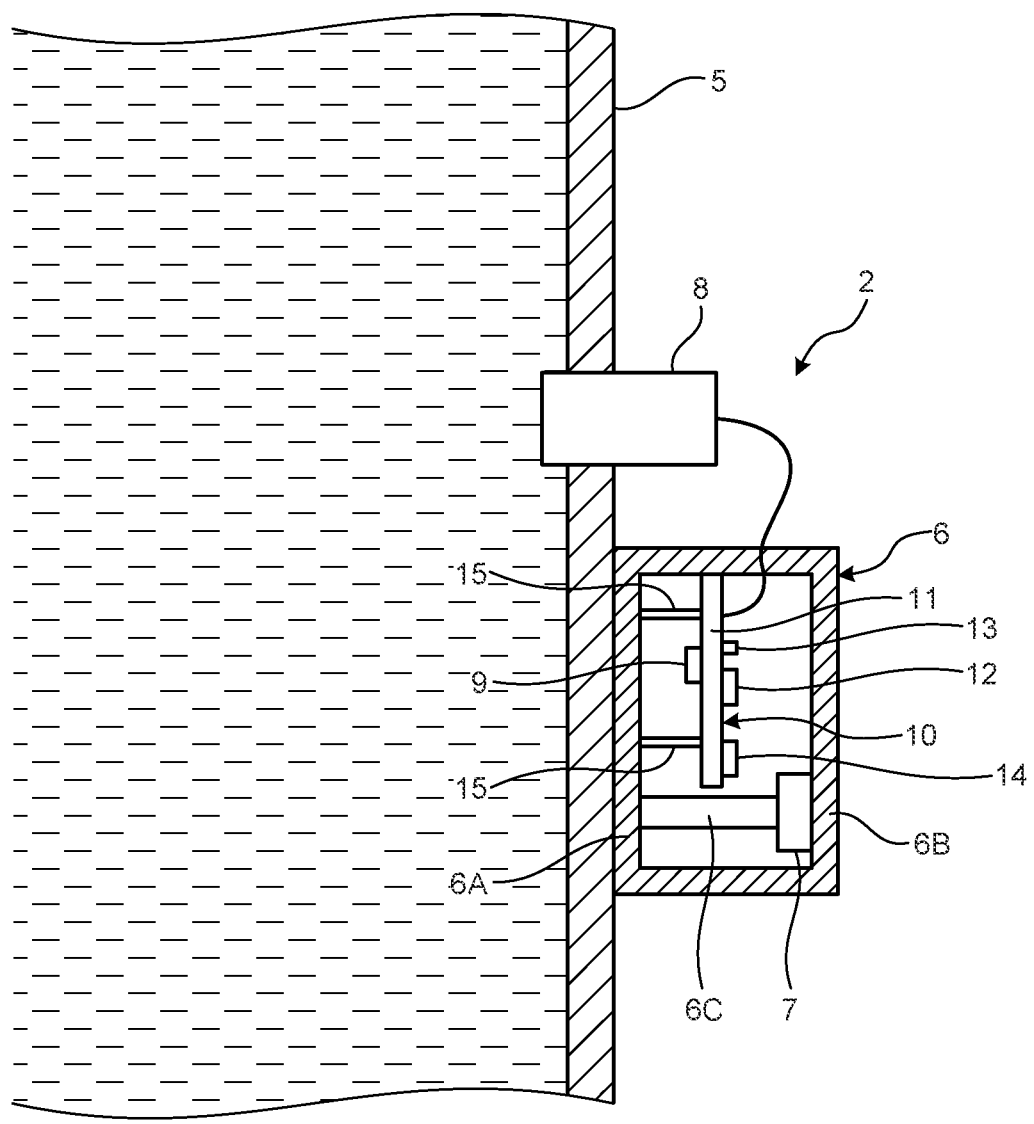
FIG. 2 is a diagram schematically illustrating a wireless terminal according to the embodiment.

FIG. 2 is a diagram schematically illustrating the wireless terminal 2 according to the embodiment. As illustrated in FIG. 2, the wireless terminal 2 includes a housing 6, an energy harvesting unit 7, an optical sensor 8, a temperature sensor 9, and a controller 10.

The housing 6 houses the energy harvesting unit 7, the temperature sensor 9, and the controller 10. The housing 6 is disposed so as to be in contact with the hydraulic device 5. The housing 6 includes a heat receiving unit 6A and a heat dissipation unit 6B. The heat receiving unit 6A is in contact with the surface of hydraulic device 5.

The energy harvesting unit 7 functions as a power source of the wireless terminal 2. The energy harvesting unit 7 generates power on the basis of a change in the environment in which the energy harvesting unit 7 is disposed. In the embodiment, the energy harvesting unit 7 is a thermoelectric power generation module. The thermoelectric power generation module generates power on the basis of heat generated by the hydraulic device 5. In the following description, the energy harvesting unit 7 is appropriately referred to as "thermoelectric power generation module 7".

The thermoelectric power generation module 7 generates power using the Seebeck effect. The hydraulic device 5 functions as a heat source of thermoelectric power generation module 7. The thermoelectric power generation module 7 is disposed between the heat receiving unit 6A and the heat dissipation unit 6B. When one end surface of the thermoelectric power generation module 7 is heated, a temperature difference is applied between the one end surface and the other end surface of the thermoelectric power generation module 7. When a temperature difference is applied between the one end surface and the other end surface of the thermoelectric power generation module 7, the thermoelectric power generation module 7 generates power. In the embodiment, the one end surface of the thermoelectric power generation module 7 is connected to the heat receiving unit 6A via a heat transfer member 6C. The other end surface of the thermoelectric power generation module 7 is connected to the heat dissipation unit 6B. The heat receiving unit 6A receives heat from the hydraulic device 5. Heat of the heat receiving unit 6A is transferred to the thermoelectric power generation module 7 through the heat transfer member 6C. The heat dissipation unit 6B receives heat from the thermoelectric power generation module 7. Heat of the heat dissipation unit 6B is discharged to the atmospheric space around the wireless terminal 2.

The optical sensor 8 detects the hydraulic oil in the hydraulic device 5. The optical sensor 8 is driven by electric power generated by the thermoelectric power generation module 7. The optical sensor 8 is disposed outside the housing 6. The optical sensor 8 is supported by at least a part of the hydraulic device 5. The optical sensor 8 and the controller 10 are connected via a cable.

In the embodiment, the optical sensor 8 detects the degraded state of the hydraulic oil. The optical sensor 8 includes an emitting unit that emits detection light and a light receiving unit that receives the detection light reflected by the hydraulic oil. When the hydraulic oil is degraded, the color of the hydraulic oil is close to black. In a case where the hydraulic oil is not degraded, the amount of detection light received by the light receiving unit increases. In a case where the hydraulic oil is degraded, the amount of detection light received by the light receiving unit decreases.

The controller 10 controls the wireless terminal 2. The controller 10 includes a circuit board 11, a microcomputer 12 mounted on the circuit board 11, a memory 13, and a wireless communication device 14 mounted on the circuit board 11. The circuit board 11 is supported by the housing 6 via support members 15.

The microcomputer 12, the memory 13, and the wireless communication device 14 are each driven by the electric power generated by the thermoelectric power generation module 7. The wireless communication device 14 communicates with the management computer 3. In the embodiment, the wireless terminal 2 and the management computer 3 communicate with each other on the basis of over the air (OTA) technology.

The temperature sensor 9 detects the temperature of the optical sensor 8 or the temperature around the optical sensor 8. In the embodiment, the temperature sensor 9 is disposed on the circuit board 11. The temperature sensor 9 may be disposed on the heat receiving unit 6A of the housing 6. The temperature sensor 9 may be disposed so as to be in contact with at least a part of the optical sensor 8. The temperature sensor 9 may be disposed so as to be in contact with the surface of the hydraulic device 5 at a position adjacent to the optical sensor 8.

Thermoelectric Power Generation Module

Figure 3:
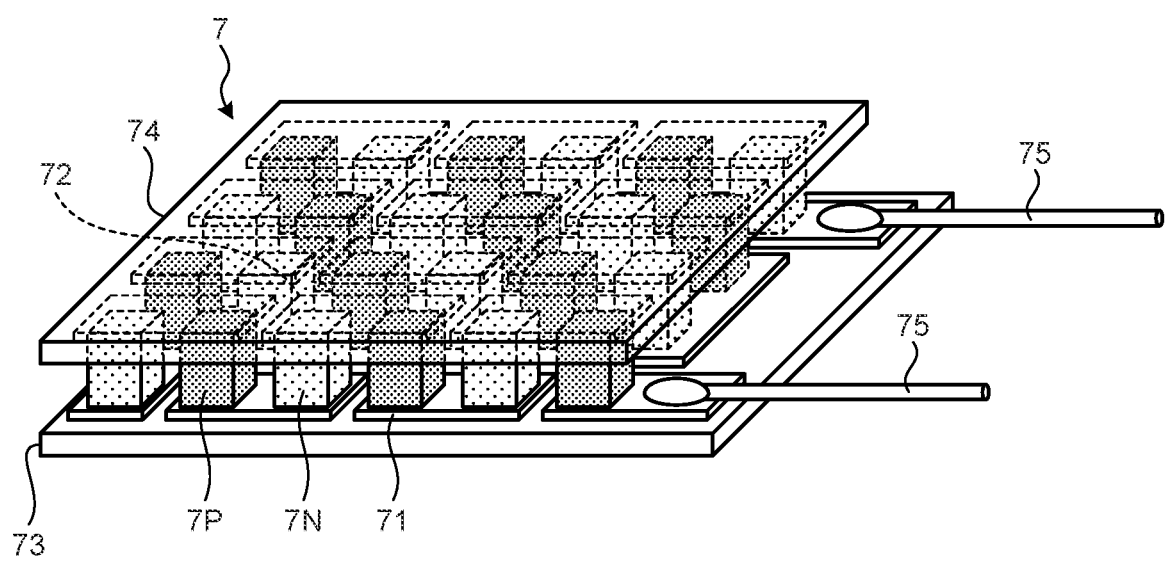
FIG. 3 is a perspective view schematically illustrating a thermoelectric power generation module according to the embodiment.

FIG. 3 is a perspective view schematically illustrating the thermoelectric power generation module 7 according to the embodiment. The thermoelectric power generation module 7 includes a p-type thermoelectric semiconductor element 7P, an n-type thermoelectric semiconductor element 7N, a first electrode 71, a second electrode 72, a first substrate 73, and a second substrate 74. The p-type thermoelectric semiconductor elements 7P and the n-type thermoelectric semiconductor elements 7N are alternately arranged in a plane parallel to the surface of the first substrate 73. The first electrode 71 is connected to each of the p-type thermoelectric semiconductor element 7P and the n-type thermoelectric semiconductor element 7N. The second electrode 72 is connected to each of the p-type thermoelectric semiconductor element 7P and the n-type thermoelectric semiconductor element 7N. One end surface of the p-type thermoelectric semiconductor element 7P and one end surface of the n-type thermoelectric semiconductor element 7N are connected to the first electrode 71. The other end surface of the p-type thermoelectric semiconductor element 7P and the other end surface of the n-type thermoelectric semiconductor element 7N are connected to the second electrode 72. The first electrode 71 is connected to the first substrate 73. The second electrode 72 is connected to the second substrate 74.

The p-type thermoelectric semiconductor element 7P and the n-type thermoelectric semiconductor element 7N each include, for example, a BiTe-based the material. The first substrate 73 and the second substrate 74 are each formed of an electrically insulating material such as ceramics or polyimide.

By heating the first substrate 73, a temperature difference is applied between one end and the other end of each of the p-type thermoelectric semiconductor element 7P and the n-type thermoelectric semiconductor element 7N. When a temperature difference is applied between one end and the other end of the p-type thermoelectric semiconductor element 7P, holes move in the p-type thermoelectric semiconductor element 7P. When a temperature difference is applied between one end and the other end of the n-type thermoelectric semiconductor element 7N, electrons move in the n-type thermoelectric semiconductor element 7N. The p-type thermoelectric semiconductor element 7P and the n-type thermoelectric semiconductor element 7N are connected via the first electrode 71 and the second electrode 72. A potential difference is generated between the first electrode 71 and the second electrode 72 by holes and electrons. As a potential difference is generated between the first electrode 71 and the second electrode 72, the thermoelectric power generation module 7 generates electric power. A lead wire 75 is connected to the first electrode 71. The thermoelectric power generation module 7 outputs electric power via the lead wire 75.

Controller

Figure 4:
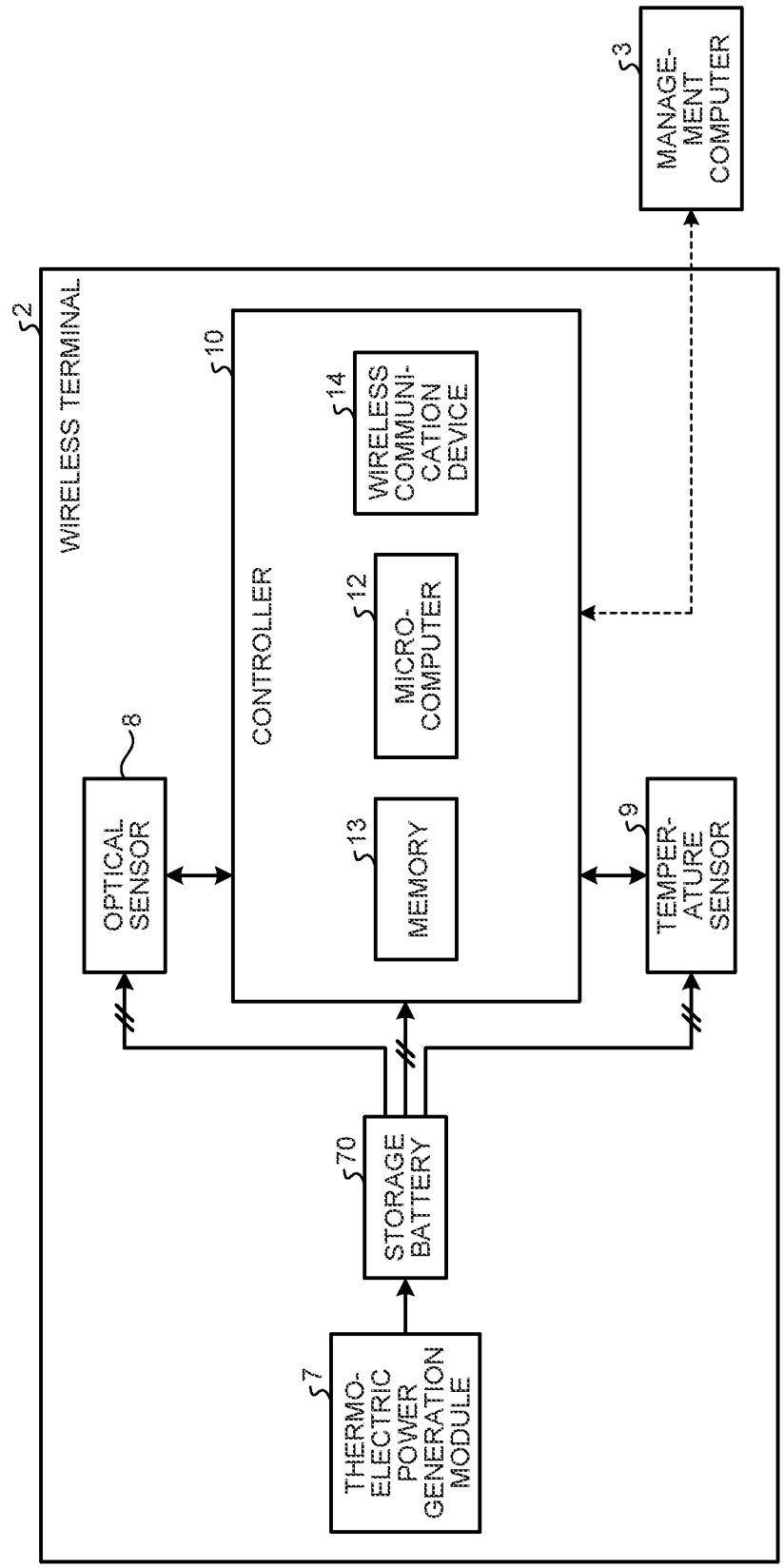
FIG. 4 is a block diagram illustrating the wireless terminal according to the embodiment.

FIG. 4 is a block diagram illustrating the wireless terminal 2 according to the embodiment. The wireless terminal 2 includes the thermoelectric power generation module 7, a storage battery 70, the optical sensor 8, the temperature sensor 9, and the controller 10.

The storage battery 70 stores the electric power generated by the thermoelectric power generation module 7. In a case where the storage amount of the storage battery 70 is larger than or equal to a predetermined first specified value, electric power is discharged from the storage battery 70. The electric power discharged from the storage battery 70 is consumed by each of the optical sensor 8, the temperature sensor 9, and the controller 10. That is, the electric power discharged from the storage battery 70 is used for driving each of the optical sensor 8, the temperature sensor 9, and the controller 10. After the electric power is discharged from the storage battery 70, the storage battery 70 stores the electric power generated by the thermoelectric power generation module 7 again.

In the embodiment, a storage state where the electric power generated by the thermoelectric power generation module 7 is stored in the storage battery 70, and a consumption state where the electric power stored in the storage battery 70 is consumed in each of the optical sensor 8, the temperature sensor 9, and the controller 10 are repeated. The storage battery 70 stores electricity intermittently. Each of the optical sensor 8, the temperature sensor 9, and the controller 10 is intermittently driven.

The controller 10 includes the microcomputer 12, the memory 13, and the wireless communication device 14.

The microcomputer 12 drives the optical sensor 8 and the temperature sensor 9 on the basis of electric power supplied from the thermoelectric power generation module 7. The microcomputer 12 acquires detection data of the optical sensor 8 and detection data of the temperature sensor 9. The microcomputer 12 performs an arithmetic process on the detection data of the optical sensor 8 to generate processing data.

The memory 13 stores parameters related to the microcomputer 12. The parameter defines an operation mode of the microcomputer 12. The parameter defines processing contents and the order of processing in the microcomputer 12. The processing of the microcomputer 12 includes an arithmetic process on the detection data of the optical sensor 8 to generate processing data. The parameter includes a coefficient used for the arithmetic process.

The microcomputer 12 operates in a predetermined operation mode on the basis of the parameter stored in the memory 13. In the embodiment, the operation of the microcomputer 12 performed on the basis of the predetermined operation mode includes an operation of driving each of the optical sensor 8 and the temperature sensor 9, an operation of acquiring the detection data of the optical sensor 8 and the detection data of the temperature sensor 9, and an operation of performing the arithmetic process on the detection data of the optical sensor 8 to generate processing data.

The wireless communication device 14 wirelessly receives a parameter change command wirelessly transmitted from the management computer 3. The management computer 3 wirelessly transmits the parameter change command and the parameter to the wireless terminal 2.

The microcomputer 12 changes the parameter stored in the memory 13 on the basis of the parameter change command wirelessly received by the wireless communication device 14. The microcomputer 12 changes the parameter stored in the memory 13 to a parameter wirelessly transmitted from the management computer 3 on the basis of the change command wirelessly received by the wireless communication device 14. In the embodiment, when the change command is wirelessly received by the microcomputer 12, the microcomputer 12 suspends the operation being performed on the basis of the operation mode and changes the parameter stored in the memory 13 on the basis of the change command. That is, when the change command is wirelessly received by the wireless communication device 14, the microcomputer 12 suspends the operation being performed on the basis of the operation mode, and then changes the parameter stored in the memory 13 during the suspension period in which driving of the optical sensor 8 is suspended.

The wireless communication device 14 can wirelessly transmit the detection data of the optical sensor 8 and the detection data of the temperature sensor 9 acquired by the microcomputer 12 to the management computer 3. The detection data of the temperature sensor 9 indicates the temperature data of the optical sensor 8. The wireless communication device 14 can wirelessly transmit the parameter stored in the memory 13 to the management computer 3. The wireless communication device 14 can also wirelessly transmit the processing data generated by the microcomputer 12 to the management computer 3.

Operation of Wireless System

Figure 5:
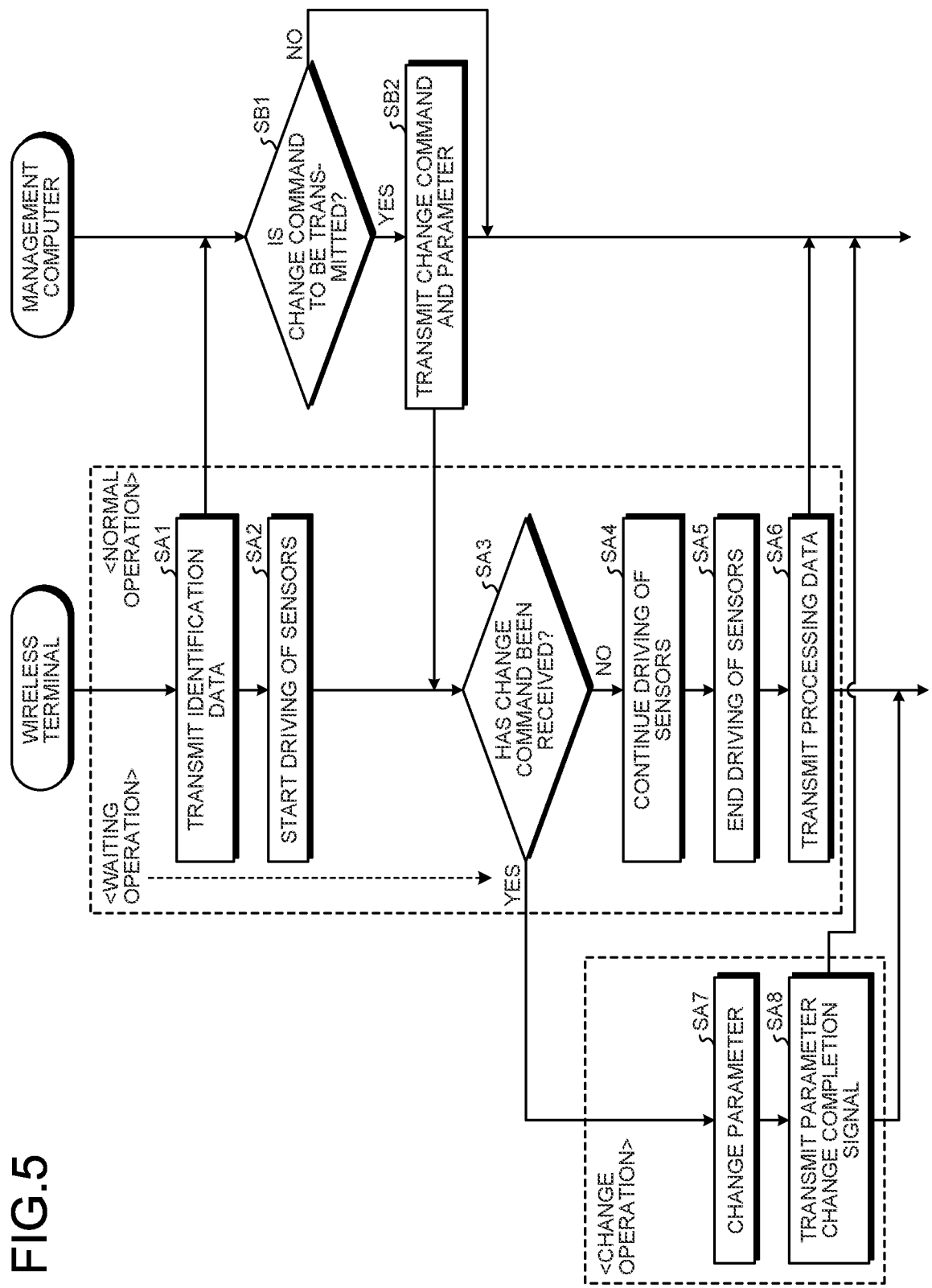
FIG. 5 is a flowchart illustrating an operation of the wireless system according to an embodiment.

FIG. 5 is a flowchart illustrating an operation of the wireless system 1 according to an embodiment.

In the embodiment, the microcomputer 12 operates in a predetermined operation mode on the basis of a parameter stored in the memory 13. The microcomputer 12 waits for an OTA command indicating a radio command from the management computer 3. In the following description, the operation performed in a predetermined operation mode on the basis of a parameter will be appropriately referred to as "normal operation", and the operation of waiting for an OTA command will be appropriately referred to as "waiting operation".

The OTA command wirelessly transmitted from the management computer 3 to the wireless terminal 2 includes a parameter change command. As described above, in a case where the wireless communication device 14 receives the parameter change command, the microcomputer 12 performs an operation of changing the parameter stored in the memory 13 to a parameter wirelessly transmitted from the management computer 3. In the following description, the operation of changing the parameter stored in the memory 13 is appropriately referred to as "change operation".

When the hydraulic device 5 is driven and a temperature difference is applied between one end surface and the other end surface of the thermoelectric power generation module 7, the thermoelectric power generation module 7 generates power. The electric power generated by the thermoelectric power generation module 7 is stored in the storage battery 70. In a case where the storage amount of the storage battery 70 is larger than or equal to a predetermined first specified value, electric power is discharged from the storage battery 70.

When electric power is discharged from the storage battery 70, the microcomputer 12 starts the normal operation and the waiting operation on the basis of the parameter stored in the memory 13.

In the embodiment, the microcomputer 12 performs the normal operation and the waiting operation in parallel. That is, the microcomputer 12 always waits for the OTA command including the change command during the period in which the normal operation is performed.

The normal operation will be described.

In the embodiment, identification data is given to each of the wireless terminals 2. Each of the wireless terminals 2 is identified by the identification data. The microcomputer 12 causes the wireless communication device 14 to transmit the identification data to the management computer 3 (step SA1).

As described with reference to FIG. 1, the management computer 3 wirelessly communicates with each of the wireless terminals 2. As the identification data is transmitted from the wireless terminal 2 to the management computer 3, the management computer 3 can identify a plurality of the wireless terminals 2. The management computer 3 can transmit the OTA command indicating a radio command to a specific wireless terminal 2 among the wireless terminals 2 on the basis of the identification data.

The microcomputer 12 starts driving each of the optical sensor 8 and the temperature sensor 9 on the basis of electric power supplied from the storage battery 70 (step SA2).

The management computer 3 determines whether to transmit a parameter change command (step SB1).

In the embodiment, whether or not the parameter needs to be changed is determined by an administrator who manages the management computer 3. An input device (not illustrated) is connected to the management computer 3. Examples of the input device include a computer keyboard and a touch panel. When determining that the parameter needs to be changed, the administrator operates the input device to generate an input signal indicating that the parameter needs to be changed. The management computer 3 determines whether to transmit the parameter change command on the basis of the presence or absence of the input signal.

In step SB1, if it is determined that the parameter change command is not transmitted (step SB1: No), the parameter is not changed.

If it is determined in step SB1 that the parameter change command is to be transmitted (step SB1: Yes), the management computer 3 transmits the parameter change command and the parameter to the wireless terminal 2 (step SB2).

The microcomputer 12 determines whether or not the wireless communication device 14 has received the parameter change command from the management computer 3 (step SA3).

If it is determined in step SA3 that the parameter change command has not been received (step SA3: No), the driving of each of the optical sensor 8 and the temperature sensor 9 is continued (step SA4).

If the storage amount of the storage battery 70 is equal to or less than a predetermined second specified value, the driving of each of the optical sensor 8 and the temperature sensor 9 is stopped (step SA5).

During a period in which each of the optical sensor 8 and the temperature sensor 9 is driven, the microcomputer 12 continues to acquire each of the detection data of the optical sensor 8 and the detection data of the temperature sensor 9 in a defined sampling cycle. The microcomputer 12 performs an arithmetic process on the detection data of the optical sensor 8 on the basis of the parameter stored in the memory 13 to generate processing data. The wireless communication device 14 transmits the processing data generated by the microcomputer 12 to the management computer 3 (step SA6).

The wireless communication device 14 transmits each of the detection data of the optical sensor 8 and the temperature data of the optical sensor 8 acquired by the temperature sensor 9 to the management computer 3.

The management computer 3 wirelessly receives the detection data of the optical sensor 8 and the temperature data of the optical sensor 8 acquired simultaneously with the detection data of the optical sensor 8.

If it is determined in step SA3 that the parameter change command is received (step SA3: Yes), the microcomputer 12 suspends the normal operation and starts the change operation.

The microcomputer 12 performs the change operation of changing the parameters stored in the memory 13 during a suspension period in which the normal operation is suspended. The microcomputer 12 changes the parameter stored in the memory 13 to the parameter transmitted from the management computer 3 on the basis of the change command from the management computer 3 (step SA7).

After the parameter change operation is completed, the microcomputer 12 causes the wireless communication device 14 to transmit a parameter change completion signal to the management computer 3 (step SA8).

The microcomputer 12 can perform the normal operation on the basis of the changed parameter.

Effects

As described above, according to the embodiment, the parameter related to the microcomputer 12 is changed on the basis of the change command transmitted from the management computer 3. As a result, the parameter can be easily changed after the wireless terminal 2 is assembled. In a case where the parameter is changed, the normal operation is suspended. As a result, the power consumption of the wireless terminal 2 is reduced in a case where the parameter related to the microcomputer 12 is changed.

In the embodiment, the microcomputer 12 performs the normal operation and the waiting operation in parallel. Since the waiting operation is performed in parallel with the normal operation, the time required for the microcomputer 12 to complete the normal operation is shortened. The power consumption of the wireless terminal 2 is thus reduced.

In the normal operation, the microcomputer 12 performs the arithmetic process on the detection data of the optical sensor 8 to generate processing data. The processing data is wirelessly transmitted from the wireless communication device 14 to the management computer 3. As a result, the management computer 3 can centrally manage the processing data transmitted from each of the wireless terminals 2. The management computer 3 can centrally manage the degraded state of the hydraulic oil in each of the hydraulic devices 5, for example.

In the embodiment, the power supply of the wireless terminal 2 is the energy harvesting unit 7. The amount of power generation of the energy harvesting unit 7 is less than, for example, the amount of electric power supplied from a commercial power supply. Since the normal operation is stopped during the period in which the parameter change operation is performed, the parameter change operation is smoothly performed in a case where the energy harvesting unit 7 with a small amount of power generation is used as the power supply.

In the embodiment, the power supply of the wireless terminal 2 includes the thermoelectric power generation module 7 that is a type of the energy harvesting unit. The electric power generated by the thermoelectric power generation module 7 is stored in the storage battery 70. In a case where the storage amount of the storage battery 70 is larger than or equal to a predetermined first specified value, electric power is discharged from the storage battery 70. The electric power discharged from the storage battery 70 is consumed by each of the optical sensor 8, the temperature sensor 9, and the controller 10.

Other Embodiments

As described above, the parameter defines the operation mode of the microcomputer 12. The parameter includes a coefficient used when the microcomputer 12 performs an arithmetic process on the detection data of the optical sensor 8 to generate processing data. The parameter stored in the memory 13 may include a correction coefficient for correcting the detection data of the optical sensor 8 that changes on the basis of the temperature of the optical sensor 8.

A phenomenon occurs in which the detection data of the optical sensor 8 changes on the basis of the temperature of the optical sensor 8. For example, a phenomenon occurs in which as the temperature of the optical sensor 8 increases, the apparent amount of detection light received by the light receiving unit of the optical sensor 8 decreases. A phenomenon occurs in which as the temperature of the optical sensor 8 decreases, the apparent amount of detection light received by the light receiving unit of the optical sensor 8 increases. In a case where the hydraulic oil is not degraded, the amount of detection light received by the light receiving unit of the optical sensor 8 increases. In a case where the hydraulic oil is degraded, the amount of detection light received by the light receiving unit of the optical sensor 8 decreases. In a case where the temperature of the optical sensor 8 is high, the optical sensor 8 may erroneously detect that the hydraulic oil is degraded although the hydraulic oil is not degraded. In a case where the temperature of the optical sensor 8 is low, the optical sensor 8 may erroneously detect that the hydraulic oil is not degraded although the hydraulic oil is degraded. By correcting the detection data of the optical sensor 8 using the correction coefficient, erroneous detection of the optical sensor 8 is substantially prevented.

The microcomputer 12 performs the arithmetic process on the detection data of the optical sensor 8 on the basis of the correction coefficient stored in the memory 13 to generate processing data. The microcomputer 12 can correct the detection data of the optical sensor 8 on the basis of the correction coefficient. The processing data generated by the microcomputer 12 includes detection data of the optical sensor 8 subjected to correction using the correction coefficient.

In the normal operation, the microcomputer 12 causes the wireless communication device 14 to wirelessly transmit the detection data of the optical sensor 8 and the temperature data of the optical sensor 8 acquired by the temperature sensor 9 simultaneously with the detection data of the optical sensor 8 to the management computer 3. The management computer 3 wirelessly receives the detection data of the optical sensor 8 and the temperature data of the optical sensor 8 acquired simultaneously with the detection data of the optical sensor 8.

The management computer 3 calculates, as a parameter, the correction coefficient for correcting the detection data of the optical sensor 8 that changes on the basis of the temperature of the optical sensor 8, on the basis of the detection data of the optical sensor 8 and the temperature data of the optical sensor 8. The correction coefficient calculated by the management computer 3 is wirelessly transmitted from the management computer 3 to the wireless terminal 2 together with a change command. The microcomputer 12 changes the correction coefficient stored in the memory 13 to the correction coefficient wirelessly transmitted from the management computer 3.

As the correction coefficient for correcting the detection data of the optical sensor 8 that changes on the basis of the temperature of the optical sensor 8 is changed on the basis of the temperature data of the optical sensor 8 acquired by the temperature sensor 9, the detection data of the optical sensor 8 is appropriately corrected. The erroneous detection of the optical sensor 8 is thus substantially prevented.

In the embodiment described above, the microcomputer 12 performs the arithmetic process on the detection data of the optical sensor 8 to generate processing data. The processing data does not need to be generated in the microcomputer 12. For example, the detection data of the optical sensor 8 and the correction coefficient stored in the memory 13 may be transmitted as a set from the wireless terminal 2 to the management computer 3. The management computer 3 may correct the detection data transmitted from the wireless terminal 2 using the correction coefficient transmitted together with the detection data in a set.

The parameter may be a correction coefficient for correcting the detection data of the optical sensor 8, a sampling frequency, or a resolution.

In the embodiment described above, the wireless terminal 2 includes the optical sensor 8 as a sensor. The wireless terminal 2 may include a vibration sensor as a sensor. The vibration sensor can detect vibrations of the hydraulic device 5. The vibration sensor may detect vibrations of a device different from the hydraulic device. Examples of the device different from the hydraulic device include a motor and a generator. Examples of the parameter related to the vibration sensor include a sampling frequency and a resolution.

The parameter related to the vibration sensor may be a type of an evaluation value related to vibration. The microcomputer 12 can calculate a plurality of evaluation values related to vibration on the basis of the detection data of the vibration sensor. Examples of the evaluation value include four types of evaluation values, that is, an overall value, a partial overall value, an effective value (root mean square value (RMS)), and a peak value. The effective value may be calculated for each of a plurality of frequency ranges obtained by dividing the entire range of a vibration waveform detected by the vibration sensor into a plurality of the frequency ranges. The effective value of vibration may be an effective value of acceleration, an effective value of speed, or an effective value of displacement. The peak value of vibration includes a maximum value and a minimum value of vibration. The peak value of vibration may be a peak value in the entire range of the vibration waveform or a peak value in each of the frequency ranges. The peak value of vibration may be a peak value of acceleration, a peak value of speed, or a peak value of displacement.

The microcomputer 12 calculates a plurality of evaluation values from the detection data of the vibration sensor on the basis of the parameter stored in the memory 13. The parameter includes the type of the evaluation value calculated by the microcomputer 12. For example, in a case where the overall value is designated as a parameter by the management computer 3 among the four types of evaluation values, that is, the overall value, the partial overall value, the effective value, and the peak value, the microcomputer 12 calculates only the overall value. The microcomputer 12 does not calculate all of the four types of evaluation values, but calculates only the evaluation value designated by the management computer 3, so that power consumption of the wireless terminal 2 is reduced.

In the embodiment described above, the wireless terminal 2 includes a sensor. However, the wireless terminal 2 does not need to include a sensor.

In the embodiment described above, the energy harvesting unit 7 may be, for example, solar power generation, vibration power generation, or electromagnetic wave power generation.

According to the present disclosure, power consumption is reduced.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A wireless terminal comprising:
a housing;
a memory disposed in the housing and configured to store a parameter in order to detect a degraded state of a hydraulic oil;
a microcomputer disposed in the housing and configured to operate in an operation mode based on the parameter;
a wireless communication device configured to wirelessly receive a change command for changing the parameter; and
a thermoelectric power generation module that is disposed inside the housing and that is in thermal contact with surfaces of the housing, the thermoelectric power generation module being configured to, based on a temperature difference between the surfaces of the housing, generate power to perform an operation by the microcomputer,
wherein the microcomputer is configured to suspend the operation based on receiving the change command and to change the parameter based on the change command,
wherein the thermoelectric power generation module is disposed between the surfaces of the housing, the surfaces of the housing comprising:

a heat receiving surface configured to be in contact with a hydraulic device and to provide heat of the hydraulic device to the thermoelectric power generation module.

2. The wireless terminal according to claim 1, further comprising a sensor,
wherein the operation of the microcomputer includes performing an arithmetic process on detection data of the sensor to generate processing data, and
wherein the wireless communication device wirelessly transmits the processing data.

3. A wireless system comprising:
the wireless terminal according to claim 1; and
a management computer that wirelessly communicates with the wireless terminal,
wherein the management computer wirelessly transmits the change command and a parameter, and
wherein the microcomputer changes the parameter stored in the memory to the parameter wirelessly transmitted from the management computer based on a basis of the change command.

4. The wireless terminal according to claim 1, further comprising a storage battery configured to store the power generated by the thermoelectric power generation module and to supply the power for operating the microcomputer.

5. The wireless terminal according to claim 4, wherein the storage battery is configured to alternate between (i) a power storage state in which the power generated by the thermoelectric power generation module and (ii) a consumption state in which the power is consumed by the microcomputer.

6. The wireless terminal according to claim 1, further comprising a heat transfer member configured to transfer heat from one of the surfaces of the housing to the thermoelectric power generation module.

7. The wireless terminal according to claim 1, the surfaces of the housing comprising:
a heat dissipation surface configured to discharge heat from the thermoelectric power generation module to an outside of the housing.

8. The wireless terminal according to claim 1, further comprising a circuit board that is disposed in the housing and supports the memory, the microcomputer, and the wireless communication device,
wherein the circuit board is spaced apart from the thermoelectric power generation module.

9. The wireless terminal according to claim 8, further comprising a support member that is disposed in the housing and supports the circuit board,
wherein the circuit board is spaced apart from the surfaces of the housing.

* * * * *